United States Patent [19]

Sugimoto et al.

[11] 4,001,223
[45] Jan. 4, 1977

[54] ADAMANTANE-PIPERAZINE DERIVATIVES

[75] Inventors: Michio Sugimoto; Fumitada Yamamoto; Kosaku Honna; Konomu Kurisaki; Hirozo Sugahara; Kiyoshi Watanabe, all of Chiba; Yasuo Fujimoto, Tokyo; Syoji Ryu, Noda, all of Japan

[73] Assignees: Idemitsu Kosan Co., Ltd.; Nippon Chemiphar Co., Ltd., both of Tokyo, Japan

[22] Filed: Dec. 16, 1975

[21] Appl. No.: 641,232

[30] Foreign Application Priority Data

| Jan. 13, 1975 | Japan | 50-5567 |
|---|---|---|
| Jan. 13, 1975 | Japan | 50-5568 |
| Jan. 13, 1975 | Japan | 50-5569 |
| Jan. 17, 1975 | Japan | 50-7065 |
| Jan. 16, 1975 | Japan | 50-6468 |
| Jan. 16, 1975 | Japan | 50-6467 |
| Jan. 14, 1975 | Japan | 50-5903 |
| Jan. 17, 1975 | Japan | 50-7066 |

[52] U.S. Cl. .................. 260/240 J; 260/240 K; 260/268 R; 260/268 C
[51] Int. Cl.² ...................... C07D 241/02
[58] Field of Search ........ 260/240 G, 240 J, 240 K, 260/268 R, 268 C, 666 M

[56] References Cited

UNITED STATES PATENTS

| 2,882,271 | 4/1959 | Janssen | 260/240 J |
|---|---|---|---|
| 3,374,244 | 3/1968 | Krimmel | 260/326.33 |
| 3,379,754 | 4/1968 | Bernstein | 260/240 G X |
| 3,573,291 | 3/1971 | Fauran et al. | 260/240 K |
| 3,624,086 | 11/1971 | Krimmel | 260/268 C X |
| 3,625,965 | 12/1971 | Irikura et al. | 260/240 K |
| 3,711,538 | 1/1973 | Narayanan | 260/240 J UX |
| 3,753,984 | 8/1973 | Fauran et al. | 260/240 J |
| 3,940,386 | 2/1976 | Szabo et al. | 260/240 K |

*Primary Examiner*—Allen B. Curtis
*Attorney, Agent, or Firm*—Flynn & Frishauf

[57] ABSTRACT

Adamantane derivatives of this invention are represented by the formula

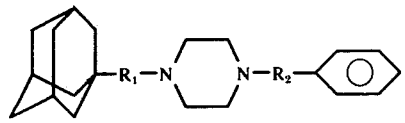

wherein $R_1$ is

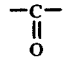

or $-CH_2-$ and $R_2$ is

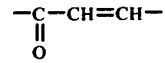

or $-CH_2CH=CH-$.

Said derivatives are cerebral vasodilators or intermediates for the same.

5 Claims, 12 Drawing Figures

ADAMANTANE-PIPERAZINE DERIVATIVES

BACKGROUND OF THE INVENTION

1. Field of the Invention

The present invention relates to novel adamantane derivatives and cerebral vasodilators containing said derivatives.

2. Description of the Prior Art

It has been known that adamantane and its derivatives are present in petroleum in nature and they have been expected as promising medicines or intermediates or synthesizing them because of their lipophilic property and low toxicity to living organisms due to their unique structural characteristics.

However, adamantane derivatives useful for medicine or intermediates therefor have not been developed up to this time.

SUMMARY OF THE INVENTION

It is an object of this invention to provide novel adamantane derivatives and cerebral vasodilators containing said derivatives.

Adamantane derivatives of this invention are represented by the formula

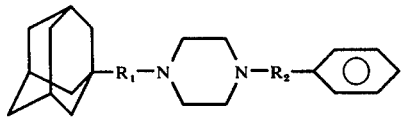

wherein $R_1$ is

or —$CH_2$— and $R_2$ is

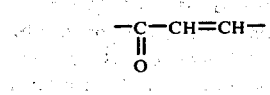

or —$CH_2$—CH=CH—.

DESCRIPTION OF THE PREFERRED EMBODIMENTS

The present invention relates to novel adamantane derivatives and cerebral vasodilators containing said derivatives. More particularly, this invention provides adamantane derivatives represented by the formula.

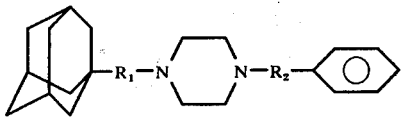

wherein $R_1$ is

or —$CH_2$— and $R_2$ is

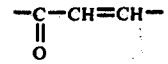

or —$CH_2$—CH=CH—, and cerebral vasodilators containing said derivatives.

The adamantane derivatives described in the present invention are the following four compounds:

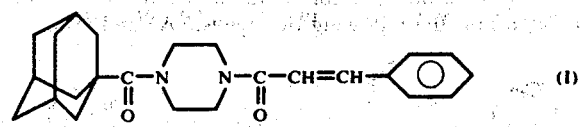 (I)

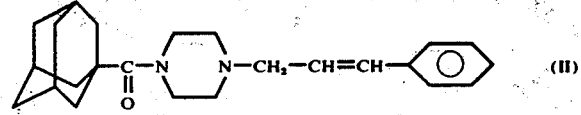 (II)

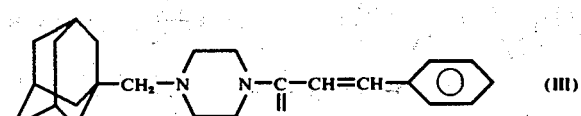 (III)

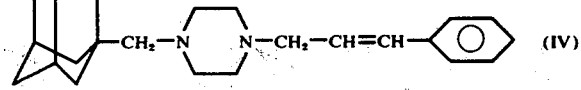 (IV)

The above-described compounds are novel, and compounds (I), (II), (III) and (IV) are N-(1-adamantane carbonyl)-N'-cinnamoyl piperazine, N-(1-adamantane carbonyl)-N'-cinnamyl piperazine, N-(1-adamantyl methyl)-N'-cinnamoyl piperazine and N-(1-adamantyl methyl)-N'-cinnamyl piperazine, respectively.

The derivatives described in the present invention can be prepared from the following compounds as the starting materials; a compound represented by the formula

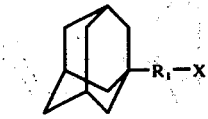

(wherein $R_1$ is

or —$CH_2$—, X is halogen and these abbreviations are used in the following sections unless otherwise stated); a compound represented by the formula

(wherein $R_2$ is

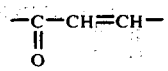

or —CH₂—CH=CH— and these abbreviations are used in the following sections unless otherwise stated), and piperazine.

In preparing said adamantane derivatives described in the present invention using the above-mentioned starting materials, possible reaction sequences can be divided into the following two types, (A) and (B).

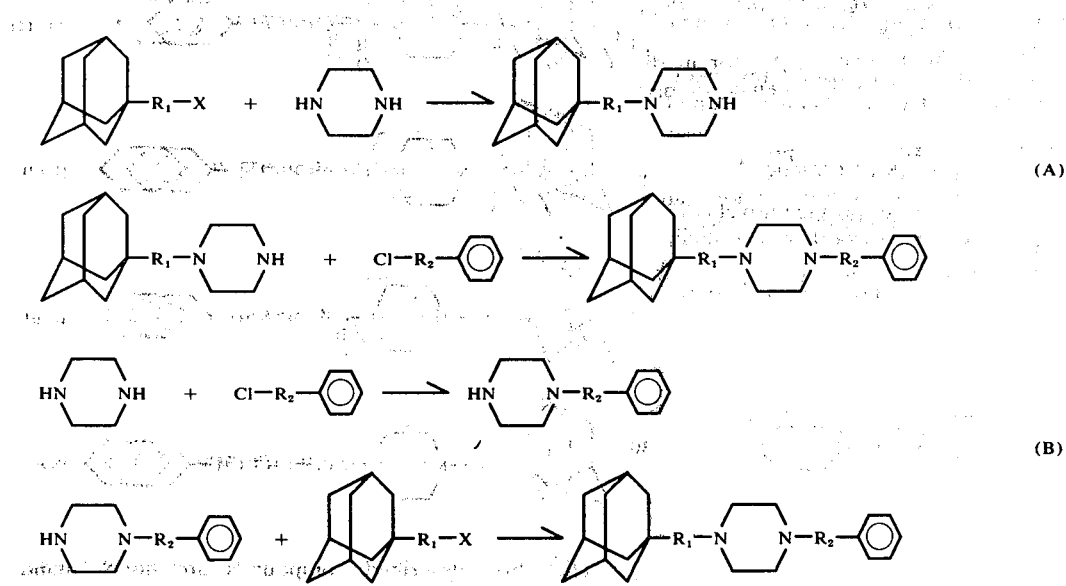

The reaction sequence (A) can be described in detail as follows. At first the following reaction in (A) is explained.

When R₁ is $$-\overset{\|}{\underset{O}{C}}-$$

synthesis of N-(1-adamantane carbonyl)-piperazine proceeds at room temperature in a solvent of halogenated hydrocarbon such as chloroform using a tertiary amine such as triethyl amine as a dehydrohalogenation agent by condensation reaction between 1-adamantyl acid halide and piperazine where the latter is added in a great excess (for example, 10 times moles over the former). In preparing 1-adamantyl acid halide, adamantane is reacted with formic acid and sulfuric acid by conventional methods to form 1-adamantyl acid which is subsequently halogenated by a halogenating agent such as thionyl chloride, phosphorous pentachloride and phosphorous pentabromide. On the other hand R₁ is —CH₂—, N-(1-adamantyl methyl)-piperazine can be obtained by condensation between 1-adamantyl methyl halides which was prepared by a reduction of 1-adamantyl acid and a subsequent halogenation and piperazine, where the latter is in excess (for example, six times molar of the former) and the reaction is carried out by heating in a solvent or without solvent. Dimethyl formamide, hexamethyl phosphoramide and the like are suitable solvents for the reaction, and the reaction proceeds at 150°–250° C for about 20 hrs. When no solvents are used, preferable reaction temperatures are 150°–300° C. Moreover, a tertiary amine such as triethyl amine can be used as a dehydrohalogenation agent. Furthermore, N-(1-adamantyl methyl)-piperazine can also be obtained by a reduction of N-(1-adamantane carbonyl)-piperazine; said reduction is carried out in a solvent of cyclic ether such as tetrahydrofuran using lithium aluminum hydride as a reducing agent at 0° C to room temperature.

Secondly, a compound thus obtained as expressed by the formula

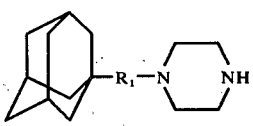

is utilized for the following reaction.

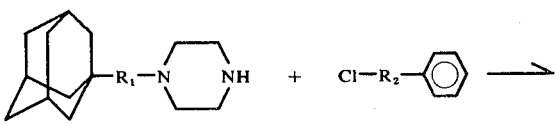

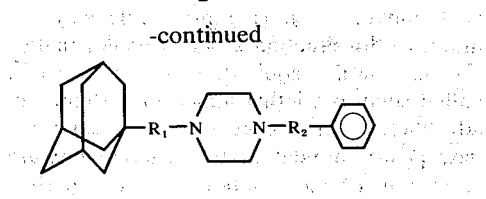

The above reaction is a condensation reaction and both starting materials are reacted in substantially equal molar quantities, but reaction can proceed even when either of them is in excess. This reaction is done preferably in a solvent whose preferable examples are a cyclic ether such as tetrahydrofuran, an alcohol such as isopropanol and a halogenated hydrocarbon such as chloroform. Furthermore, in this reaction a dehydrohalogenation agent is not necessarily required. However, use of a tertiary amine such as triethyl amine as a dehydrohalogenation agent is advantageous in order to increase reaction rate or facilitate post-treatment of the reaction mixture such as separation of the reaction product. In this case the amount of a dehydrohalogenation agent is preferably 1 to 1.5 times molar of the product. Definite conditions for condensation described above should be determined according to the nature of $R_1$ and $R_2$ and subsequent sections will describe four types of reaction conditions in detail.

When $R_1$ is

and $R_2$ is

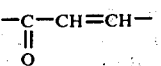

namely in a preparation of a novel compound, N-(1-adamantane carbonyl)-N'-cinnamoyl piperazine (I) from N-(1-adamantane carbonyl)-piperazine and cinnamoyl chloride, it is preferable to use a halogenated hydrocarbon such as chloroform as a solvent. Moreover, the reaction temperature is set at 0° C to room temperature and the amount of cinnamoyl chloride is set at 1.4 times molar of N-(1-adamantane-carbonyl)-piperazine. Quantitative recovery of the product can be attained by completing the reaction by refluxing. After completing the reaction, separation of the product, N-(1-adamantane carbonyl)-N'-cinnamoyl-piperazine (I), from the reaction mixture can be made by conventional manner, for example filtering the reaction mixture and the filtrate thus obtained is washed with an alkaline solution and water, and after drying, solvent is distilled away. Subsequently, the solid thus recrystalized is from methanol to obtain a purified product.

When $R_1$ is

and $R_2$ is —CH$_2$—CH=CH—, namely in preparation of a novel compound, N-(1-adamantane carbonyl)-N'-cinnamyl piperazine (II), from N-(1-adamantane carbonyl)-piperazine and cinnamyl halide, it is preferable to use an alcohol such as isopropanol as a solvent. Moreover, the reaction proceeds efficiently at room temperature and the amount of cinnamyl halide is set at 1.4 molar times of N-(1-adamantane carbonyl)-piperazine. The reaction is preferably carried out under refluxing. After completing the reaction, separation of the product, N-(1-adamantane carbonyl)-N'-cinnamyl piperazine (II), from the reaction mixture can be made by conventional manner, for example precipitation of reaction mixture, filtration and then distilling solvent away. The residues are dissolved in chloroform and then subjected to silica gel column chromatography. The product thus obtained is recrystalized from ethanol.

When $R_1$ is —CH$_2$— and $R_2$ is

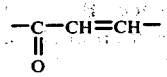

namely in a preparation of a novel compound, N-(1-adamantyl methyl)-N'-cinnamoyl piperazine (III), from N-(1-adamantyl methyl)-piperazine and cinnamoyl halide it is preferable to use a cyclic ether such as tetrahydrofuran as a solvent and the product can be obtained efficiently by reacting the above starting materials for 2 hours at room temperature. After completing the reaction, separation of this product, N-(1-adamantyl methyl)-N'-cinnamoyl piperazine (III), from the reaction mixture can be made by conventional manner, for example precipitation and filtration of the reaction mixture and then the filtrate is washed with an alkaline solution and water. Subsequently the product hydrating and then solvent is distilled away. The product thus obtained is recrystallized from ethanol.

When $R_1$ is —CH$_2$— and $R_2$ is —CH$_2$—CH=CH—, namely in a preparation of a novel compound, N-(1-adamantyl methyl)-N'-cinnamyl piperazine (IV), from N-(1-adamantyl methyl)-piperazine and cinnamyl halide, it is preferable to use an alcohol such as isopropanol as a solvent. Molar ratio of N-(1-adamantyl methyl)-piperazine and cinnamyl halide is set preferably at almost one and the reaction time and temperature for condensation without solvent are 3 hrs and 50°–100° C., respectively, when the reaction is carried out in a solvent, both starting materials are mixed at a temperature of below room temperature and then the reaction temperature is raised to refluxing temperature as proceeding of the reaction process to complete the reaction. In this case, about 5 hours are sufficient for the reaction. Separation of the product can be carried out by conventional manner. For instance, when condensation reaction is made without a solvent and a dehydrohalogenation agent, extraction with chloroform after alkaline treatment is done and then the product is subjected to silica gel column chromatography for purification. When the reaction is carried out without using a solvent but with a dehydrohalogenation agent, the reaction product is dissolved in chloroform, washed with water and after drying and concentration, the product is subjected to column chromatography of silica gel to purify. Moreover, when the reaction is carried out in a solvent, the solvent is distilled away and then the above-described methods are successfully applied to purify the product.

The compounds used in the above reaction represented by the formula

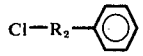

are actually cinnamoyl chloride and cinnamyl chloride which are known compounds. Thus these compounds are commercially available or can be prepared by conventional methods as follows; cinnamoyl chloride can be prepared through Claisen condensation between benzaldehyde and acetoaldehyde to provide cinnamic aldehyde which is then oxidized and chlorinated. On the other hand, cinnamyl chloride can be prepared through Claisen condensation as described above to obtain cinnamic aldehyde which is then reduced and chlorinated.

The reaction sequence (B) is explained in detail. At first the following reaction in (B) is explained.

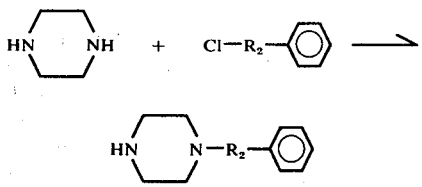

This reaction is a known reaction and the reaction is carried out in a solvent such as isopropanol, chloroform and dichloromethane where the ratio of piperazine to a compound represented by the formula

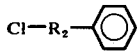

(actual examples are cinnamoyl chloride and cinnamyl chloride) is equimolar or in large excess of piperazine (6-10 times molar). The reaction proceeds efficiently at room temperature.

Secondly, a compound thus obtained as expressed by the formula

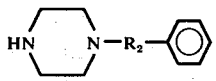

is utilized for the following reaction.

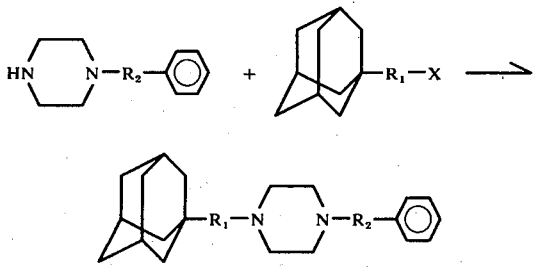

The above reaction is a condensation reaction and both starting materials are reacted in substantially equal molar quantities, but the reaction can proceed even when either of them is in excess. This reaction is done preferably in a solvent. In this case, a cyclic ether such as tetrahydrofuran is a preferable solvent. Furthermore, in this reaction a dehydrohalogenation agent is not necessarily required. However, use of a tertiary amine such as triethyl amine or sodium carbonate is advantageous in order to increase reaction rate or facilitate post-treatment of the reaction mixture such as separation of the reaction product. In this case, an amount of a dehydrohalogenation agent is preferably 1-1.5 times molar of the product. Concrete conditions for condensation described above should be determined according to the nature of $R_1$ and $R_2$ and subsequent sections describe four types of reaction conditions in detail.

When $R_1$ is

and $R_2$ is

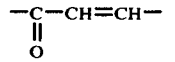

namely in preparation of N-(1-adamantane carbonyl)-N'-cinnamoyl piperazine (I) from 1-adamantyl acid halide and N-cinnamoyl piperazine, it is preferable to carry out reaction in the presence of a tertiary amine such as triethyl amine as a dehydrohalogenation agent. Moreover, this condensation reaction is carried out in a cyclic ether such as tetrahydrofuran and is completed within about 30 minutes at below 10° C. Separation of the product can be made be conventional manner, for example washing with an alkaline solution and washing with water and then separating an ether layer. After drying, ether is distilled off to make chloroform solution which is subjected to silica gel column chromatography to purify the product.

When $R_1$ is

and $R_2$ is —$CH_2$—CH=CH—, namely in a preparation of N-(1-adamantane carbonyl)-N'-cinnamyl piperazine (II) from 1-adamantyl acid halide and N-cinnamyl piperazine, it is advantageous to carry out reaction in a cyclic ether such as tetrahydrofuran and in the presence of triethyl amine as a dehydrohalogenation agent, as shown in the case of condensation between 1-adamantyl acid halide and N-cinnamoyl piperazine. The reaction proceeds efficiently at around room temperature and is completed within 2 hours. Separation of the product from the reaction mixture can be carried out by the same method as described in the case of N-(1-adamantane carbonyl)-N'-cinnamoyl piperazine (I) as shown above.

When $R_1$ is —$CH_2$— and $R_2$ is

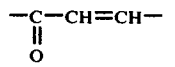

namely in preparation of N-(1-adamantyl methyl)-N'-cinnamoyl piperazine (III) from 1-adamantyl methyl halide and N-cinnamoyl piperazine, the reaction proceeds efficiently without solvent, but reaction temperatures of 150°–300° C are preferable. In this case, sodium carbonate is a preferable dehydrohalogenation agent and it is preferable to carry out the reaction in a sealed tube or sealed reaction system, since 1-adamantyl methyl halide is sublimed. In this condensation reaction, a good yield of the product can be obtained about 10 hours. Separation of N-(1-adamantyl methyl)-N'-cinnamoyl piperazine (III) from the reaction mixture can be done by preparing a chloroform solution of the reaction mixture and processing similarly to the method as shown above.

When $R_1$ is —$CH_2$— and $R_2$ is —$CH_2$—$CH$=$CH$—, namely in a preparation of a new compound, N-(1-adamantyl methyl)-N'-cinnamyl piperazine (IV) from 1-adamantyl methyl halide and N-cinnamyl piperazine, the reaction can be carried out with or without solvent. When the reaction is carried out without solvent, the reaction temperature should be set at 150°–300° C, and preferably at about 200° C and it is possible to use sodium carbonate or a tertiary amine as a dehydrohalogenation agent when required. Since 1-adamantyl methyl halide is sublimed, it is generally preferable to carry out the reaction in a sealed tube or sealed reaction system.

As indicated in the foregoing sections, novel adamantane derivatives (I), (II), (III) and (IV) can be prepared through the reaction sequences (A) or (B).

Novel adamantane derivatives (I), (II) and (III) prepared by the present invention, namely N-(1-adamantane carbonyl)-N'-cinnamoyl piperazine, N-(1-adamantane carbonyl)-N'-cinnamyl piperazine and N-(1-adamantyl methyl)-N'-cinnamoyl piperazine, provide the adamantane derivative (IV), N-(1-adamantyl methyl)-N'-cinnamyl piperazine, by transforming their carbonyl group into a methylene group with a reducing agent. This adamantane derivative (IV) shows very low toxicity and has a smooth muscle relaxing action, especially as an excellent cerebral vasocilator. Therefore, it can be said that all the novel adamantane derivatives (I), (II) and (III) are useful intermediates for the synthesis of an excellent medicine, the adamantane derivative (IV). The reduction reaction of the above-described adamantane derivatives (I), (II) and (III) is to reduce one or two amide carbonyl groups in those derivatives to a methylene group and a reducing agent to be used in the present reduction must be those that reduce only an amide carbonyl group without reducing double bonds between carbon atoms. A preferable example of a reducing agent employed is lithium aluminum hydride and in this case a cyclic ether such as tetrahydrofuran is generally used as a solvent. The reaction temperature is 0° C to a room temperature as in conventional methods and is raised to refluxing temperature as the reaction proceeds. Moreover, it can be noted as another reducing method that an amidocarbonyl group can be treated with phosphorous pentasulfate and potassium sulfate and then the thioamide group thus obtained is reduced by electrolytic reduction or reductive desulfuration.

The novel adamantane derivative (IV), N-(1-adamantyl methyl)-N'-cinnamyl piperazine which is prepared by reduction of the above-described adamantane derivatives or by the reaction sequences (A) or (B) shows very excellent pharmacological effects as described in the foregoing sections. We examined its pharmacological effect, toxicity and chemical characteristics and found that the novel compound shows an action increasing cerebral blood flow and a smooth muscle relaxing action and possesses low toxicity and good stability against heat, alkali and acid.

N-(1-adamantyl methyl)-N'-cinnamyl piperazine having the good characteristics as described above is very useful as a medicine, especially as a cerebral vasodilator. Furthermore, it was found that this compound is very safe to the human body, since this shows very low toxicity compared with conventional cerebral vasodilators, little side effects such as an excessive hypotension. In addition, an action increasing blood flow of cerebral cortex is significant and it exhibits similar action also on muscular blood flow, especially blood flow of gastrocnemius muscle. This novel compound can be said to be appropriate for pharmaceutical products, because it shows high stability against heat, alkali and acid. Therefore, this compound, N-(1-adamantyl methyl)-N'-cinnamyl piperazine, is widely and effectively used as a therapeutic for cerebral apoplexy and in treatment of various symptoms such as cerebral angiopathy, cephalic trauma sequela, etc. in the practical field.

The present invention is further illustrated in the following examples.

EXAMPLE 1

Synthesis of N-(1-adamantane carbonyl)-N'-cinnamoyl piperazine

I. Preparation of starting materials

1. Preparation of 1-adamantyl acid

To a 10 liter three necked flask, 2350 g (24 moles) of 98% sulfuric acid, 500 ml of carbon tetrachloride and 68 g (0.5 moles) of adamantane were added and mixed well, and then 5 ml of 98% formic acid were added to the flask while cooling with ice to 17°–19° C. Subsequently, a solution of 148 g (190 ml, 2 moles) of t-butyl alcohol dissovled in 275 g (6 moles) of 98–100% formic acid was added dropwise to the flask. Dropwise addition was completed in 2 hrs. while the temperature was kept at 17°–25° C. Stirring of the mixture was continued for another 30 min. and then 3500 g of crushed ice were added. Water layer separated from an organic solvent layer was extracted three times with 500 ml of carbon tetrachloride. Combined carbon tetrachloride layers were washed with 550 ml of 15 N ammonium hydroxide and then filtered with a Buchner funnel to obtain 1-adamantyl acid ammonium salt. The solid thus obtained was washed with 100 ml of cold acetone and suspended in 1250 ml of water to which 125 ml of 12 N—HCl was added, and then extracted with 500 ml of chloroform. Chloroform layer was dehydrated with anhydrous sodium sulfate and filtered, and then the solvent was distilled away to obtain about 80 g of crude 1-adamantyl acid. This crude preparation was recrystallized from methanol-water (3:1) and 68 g of 1-adamantyl acid were obtained. Melting point of 1-adamantyl acid thus obtained was 175°–177° C and yield was 75%

2. Preparation of 1-adamantyl acid chloride

To 18 g of 1-adamantyl acid obtained by the method described in (1), 50 ml of thionyl chloride were added while cooling and after the mixture was refluxed with heating for 30 min., excess thionyl chloride was distilled away in vacuo. Subsequently, 30 ml portions of dehydrated benzene were added twice to remove thionyl chloride up to trace amounts and then was distilled away by adding 30 ml of absolute ether. Through the processes described above, 19.2 g of 1-adamantyl acid chloride were obtained as a brownish white solid. Melting point of the product was 46°–47° C and the yield was about 92%.

3. Preparation of N-(1-adamantane carbonyl)-piperazine

Absolute piperazine (21.67 g) was dissolved in 30 ml of chloroform and the chloroform solution (20 ml) of 1-adamantyl acid chloride obtained in (2) was added dropwise with stirring the mixture at ordinary temperature. After mixing was continued for another 2 hours, precipitates were filtered and then the filtrate was washed with 5% sodium hydroxide (50 ml) and subsequently with 200 ml of water. After the resulting chloroform layer was dehydrated, chloroform was distilled away. The residues were subjected to silica gel column chromatography (eluants were mixtures of chloroform and methanol). Melting point of N-(1-adamantane carbonyl)-piperazine obtained was 134°–136° C and the yield was 60%.

4. Preparation of cinnamoyl piperazine

Absolute piperazine (206 g) was dissolved in 500 ml of chloroform and 66.3 g of cinnamoyl chloride was added gradually at 0° C while mixing. The addition required 3 hours. After mixing was continued for another 2 hr., precipitates were filtered and then the filtrate (chloroform layer) was washed with 50 ml of 5% sodium hydroxide and 50 ml of water. The residues obtained after solvents were distilled away in vacuo were subjected to silica gel column chromatography (eluants were mixtures of chloroform and methanol). Thus crystalline N-cinnamoyl piperazine was obtained. Melting point of the product was 30°–40° C and the product was very hygroscopic. The yield was 30%.

II. Preparation of N-(1-adamantane carbonyl)-N'-cinnamoyl piperazine

1. N-(1-adamantane carbonyl)-piperazine (0.5 g) obtained in (1) and (3) of the section (I) and 0.3 ml of triethylamine were dissolved in 20 ml of chloroform and then 10 ml of chloroform containing 0.47 g of cinnamoyl chloride were added dropwise at 0° C while mixing. After the completion of dropwise addition, the reaction was continued for 4.5 hrs. under refluxing and then the temperature brought up to room temperature. After eliminating precipitates by filtration, the filtrate was washed with 5% sodium hydroxide and water. After washing, it was dehydrated and the solvent was distilled away. The product was recrystallized from methanol and pale yellow crystalline N-(1-adamantane carbonyl)-N'-cinnamoyl piperazine was obtained. Melting point of the product was 220° C and the yield was about 100%.

2. N-cinnamoyl piperazine (1 g) obtained in (4) of (I) and 0.47 g of triethylamine were dissolved in 15 ml of tetrahydrofuran and then 15 ml of tetrahydrofuran containing 0.9 g of the 1-adamantyl acid chloride obtained in (2) of (I) were added dropwise. After mixing for 2 hours, precipitates were removed by filtration. Subsequently, the filtrate was washed with 50 ml of 5% sodium hydroxide and 50 ml of water and after dehydration, solvents were distilled away. The solid thus obtained was recrystallized from methanol and pale yellow crystalline N-(1-adamantane carbonyl)-N'-cinnamoyl piperazine was obtained. Melting point of the product was 220° C and the yield was about 100%.

III. Analysis of N-(1-adamantane carbonyl)-N'-cinnamoyl piperazine

Analytical data of N-(1-adamantane carbonyl)-N'-cinnamoyl piperazine obtained in (II) were as follows. FIGS. 1, 2 and 3 illustrates Mass spectrum, Infra Red (IR) absorption spectrum and Nuclear Magnetic Resonance (NMR) spectrum of the said compound respectively.

| (a) | Elementary analysis | | |
| --- | --- | --- | --- |
| | | Calculated for $C_{24}H_{30}N_2O_2$ | Found |
| | C: | 76.15% | 74.9% |
| | H: | 7.99% | 8.5% |
| | N: | 7.40% | 7.2% |
| (b) | Mass spectrum | | |
| | Calculated | 378 | |
| | Found Mass No. $M^+$ | 378 | | c. IR absorption spectrum (KBr pellet)
1650, 1610 cm$^{-1}$ (amide), 1600, 1580, 1400, 1010 cm$^{-1}$ (phenyl), 970 cm$^{-1}$

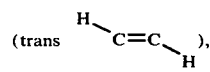
(trans)

760, 700 cm$^{-1}$ (mono-substituted phenyl), 1420, 1350, 1160 cm$^{-1}$ (adamantane)

d. NMR spectrum (solvent: CDCl$_3$)
8.24 τ (s. 6H, δ-CH$_2$), 7.96 τ (s. 9H, β-CH$_2$+γ-CH), 6.26 τ (s. 8H, a-CH$_2$+b-CH$_2$), 3.08 τ (d. J=16 Hz, 1 H, H$_{(2)}$), 2.26 τ (d. J=16 Hz, 1 H, H$_{(1)}$), 2.50 τ (m. 5 H, phenyl)

e. Structure
From the results shown above, the structure of the compound can be deduced as follows:

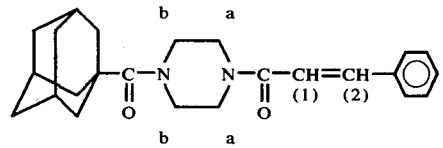

f. Melting point: 220° C

EXAMPLE 2

Synthesis of N-(1-adamantane carbonyl)-N'-cinnamyl piperazine

I. Preparation of starting materials

1. Preparation of N-cinnamyl piperazine

Absolute piperazine (217 g, 2.5 moles) was dissolved in 1 liter of isopropanol and 72.6 g of cinnamyl chloride (0.5 moles) were added dropwise gradually at room temperature without mixing. After the completion of dropwise addition, it was heated at 70° C for 3 hrs. with mixing. After the solvent was distilled away, the reaction mixture was dissolved in 500 ml of chloroform and then washed with sodium hydroxide and water. Subsequently, it was dried over potassium carbonate and then was filtered. Chloroform was distilled away in vacuo. By Subliming the mixture obtained, piperazine was removed and then the residues were distiled to obtain N-cinnamyl piperazine. The product was crystallized and then was recrystallized from n-hexane. Boiling point of the product was 162°–165° C (4 mmHg). Melting point was 31°–33° C and the yield was 56%.

II. Preparation of N-(1-adamantane carbonyl)-N'-cinnamyl piperazine

1. N-(1-adamantane carbonyl)-piperazine (0.5 g) which was obtained in (3) of (I) of Example 1 and 0.3 ml of triethylamine were dissolved in 10 ml of isopropanol and mixed well, and subsequently 0.46 g of cinnamyl chloride were added gently without mixing. The reaction was carried out for 10 hrs. under refluxing. Subsequently, precipitates were removed by filtration and isopropanol was distilled away in vacuo. The residues were dissolved in chloroform, which was washed with water and dehydrated. After chloroform was distilled away, residues were subjected to silica gel column chromatography (eluants were mixtures of chloroform and methanol) and N-(1-adamantane carbonyl)-N'-cinnamyl piperazine thus obtained was recrystallized from ethanol. Melting point of the product was 108°–109° C and the yield was 41%.

2. N-cinnamyl piperazine (17 g, 0.084 moles) which was obtained in (1) of (I) and 10.3 g (0.101 mole) of triethylamine were dissolved in 500 ml of tetrahydrofuran and the solution of tetrahydrofuran containing 20 g (0.101 mole) of 1-adamantyl acid chloride obtained in Example 1, I(2) was added dropwise at 0° C with stirring. After mixing for another 2 hrs. at room temperature, precipitates were removed by filtration and the filtrate was washed with 300 ml of water, 300 ml of 5% sodium hydroxide and 300 ml of water in this order. The solution was dehydrated and filtered, and then the solvent was distilled away. Solid N-(1-adamantane carbonyl)-N'-cinnamyl piperazine thus obtained was recrystallized from ethanol. Melting point of the product was 108°–109° C and the yield was 95%.

III. Analyses of N-(1-adamantane carbonyl)-N'-cinnamyl piperazine

Analytical data of N-(1-adamantane carbonyl)-N'-cinnamyl piperazine obtained in (2) of (II) were as follows. FIGS. 4, 5 and 6 illustrate mass spectrum, IR absorption spectrum and NMR spectrum, respectively.

| (a) | Elementary analysis | | |
|---|---|---|---|
| | | Calculated | Found |
| | C: | 79.08% | 78.40% |
| | H: | 8.85% | 8.83% |
| | N: | 7.69% | 7.56% |
| (b) | Mass spectrum | | |
| | Calculated | | 364 |
| | Found Mass No. M+ | | 364 | c. IR absorption spectrum (KBr pellet)
1620 cm$^{-1}$ (amide), 1600, 1595, 1500, 1450, 1020 cm$^{-1}$ (phenyl), 970 cm$^{-1}$ (trans 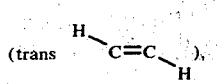 ), 750, 700 cm$^{-1}$ (mono-substituted phenyl), 1410, 1350, 1150 cm$^{-1}$ (adamantane)

d. NMR spectrum (solvent: CDCl$_3$)
8.28 τ(s. 6H, δ-CH$_2$), 8.00 τ(s. 9H, β-CH$_2$ + γ-CH), 7.55 τ(t. J=4.0 Hz, 4H, a-CH$_2$), 6.86 τ(d. J=6.0 Hz, 2H, —CH$_2$—N), 6.30 τ(t. J=4 Hz, 4H, b-CH$_2$), 3.70 τ(m. 2H, vinyl), 2.70 τ(m. 5H, phenyl)

e. Structure

From the results shown above, the structure of the compound can be deduced as follows:

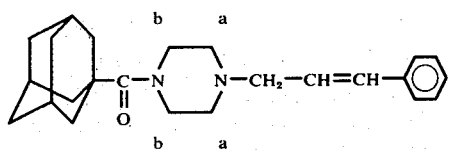

f. Melting point: 108°–109° C

EXAMPLE 3

Synthesis of N-(1-adamantyl methyl)-N'-cinnamoyl piperazine

I. Preparation of starting materials

1. Preparation of adamantyl methylalcohol

To 500 ml of dehydrated ether, 15 g of lithium aluminum hydride were added and mixed and then the solution which was prepared by dissolving 54 g (0.3 mole) of 1-adamantyl acid prepared in Example 1 (I), (1) into 500 ml of dehydrated ether was added dropwise at a rate that can maintain moderate refluxing (about 2.5 hrs). After the completion of dropwise addition, refluxing is continued for another 2 hours. Subsequently, the mixture was cooled to room temperature and to this, 75 ml of distilled water were added carefully followed by addition of 300 ml of 5 N sulfuric acid and 500 ml of ether. After separating the resulting ether layer, water layer was extracted with 300 ml of ether once. Pooled ether layers were washed with water, water saturated with sodium bicarbonate and water in this order, and then were dehydrated with anhydrous magnesium sulfate. The ether layer was evaporated and the solid obtained was recrystallized from water-methanol. Thus 47 g of 1-adamantyl methylalcohol were obtained. Melting point of 1-adamantyl methylalcohol thus obtained was 114°–116° C and the yield was 94%.

2. Preparation of 1-adamantyl methyl bromide

To 39 g (0.17 moles) of zinc bromide, 29.8 g (0.17 mole) of hydrobromic acid were added. To the solution thus obtained, 11.5 g (0.069 mole) of 1-adamantyl methylalcohol which was prepared by the method shown in (1) was added and the mixture was refluxed for 11 hours. After the reaction mixture was brought to room temperature, 200 ml of water were added to this and extracted with two 300 ml portions of ether. After washing with 100 ml of water saturated with sodium bicarbonate and 100 ml of water, the resulting ether layer was dehydrated with anhydrous magnesium sulfate and was filtered. Ether was then distilled away. Residual solids were recrystallized from methanol or sublimed (1 mmHg, 75° C) to purify it, and 13 g of 1-adamantyl methyl bromide were obtained. Melting point of the product was 37°–39° C and the yield was 84%.

3. Preparation of 1-adamantyl methyl chloride

Chlorination reaction of 1-adamantyl methylalcohol which was obtained by the same method described in (1) was carried out under the same conditions for the bromination reaction shown in (2) except that zinc bromide and hydrobromic acid were replaced by zinc chloride and hydrochloric acid respectively. The product was purified by recrystallized from methanol. Melting point of 1-adamantyl methyl chloride thus obtained was 32°–34° C and the yield was 91%.

4. Preparation of N-(1-adamatyl methyl)-piperazine

To a 10 ml autoclave, 0.5 g (0.0022 moles) of 1-adamantyl methyl bromide obtained in (2) and 1.13 g (0.013 mole) of absolute piperazine was added and the atmosphere was replaced with argon, and then the autoclave was heated at 200° C in an oil bath for 20 hrs. After it was cooled to room temperature, the contents were dissolved in chloroform (100 ml) which was then washed with 20 ml of water and dehydrated with anhydrous magnesium sulfate. After filtration, chloroform was distilled away. The sample thus obtained was subjected to silica gel column chromatography for purification (eluants were mixture of chloroform and methanol).

Resulting N-(1-adamantyl methyl)-piperazine was recrystallized from acetone. Melting point of the product was 107°–109° C and the yield was 58%.

II. Preparation of N-(1-adamantyl methyl)-N'-cinnamoyl piperazine

1. N-(1-adamantyl methyl)-piperazine (4.6 g, 0.02 mole) obtained in (4) of (I) and 2 g (0.02 mole) of triethylamine were dissolved in 100 ml of tetrahydrofuran and tetrahydrofuran solution (40 ml) containing 3.3 g (0.02 moles) of cinnamoyl chloride was added dropwise to the solution filtration 0° C. After mixing was continued for another 2 hrs., precipitates were removed by filteration and the filtrate was washed with 100 ml of water, 150 ml of 5% sodium hydroxide and 100 ml of water in this order. After dehydration, the solvent was distilled away in vacuo and crystalline N-(1-adamantyl methyl)-N'-cinnamoyl piperazine was obtained by recrystallization from ethanol. Melting point of the product was 123°–125° C and the yield was 70%.

2. N-cinnamoyl piperazine (0.5 g, 0.0023 mole) which was obtained in Example 1, (I)(4), 0.52 g (0.0023 mole) of 1-adamantyl methyl bromide which was obtained in (I)(2) of this example, and 0.24 g (0.0023 mole) of anhydrous sodium carbonate were place in 10 ml autoclave the atmosphere of which was then replaced by argon and the reaction was carried out at 200° C for 24 hours. After it was cooled to room temperature, 20 ml of chloroform were added and after washing, chloroform was distilled away. The residues thus obtained were subjected to silica gel column chromatography (eluants: mixtures of chloroform and methanol) and N-(1-adamantyl methyl)-N'-cinnamoyl piperazine obtained was recrystallized from ethanol. Moreover, 29% of 1-adamantyl methyl bromide was also recovered. Melting point of the product was 123°–125° C and the yield was 51%.

3. The same procedures as described in (2) of (II) were carried out except that 1-adamantyl methyl bromide which was obtained in (II), (2) was replaced by 1-adamantyl methyl chloride which was obtained in (I), (3) and N-(1-adamantyl methyl)-N'-cinnamoyl piperazine was obtained with a yield of 18%. Furthermore, 70% of of 1-adamantyl methyl chloride was recovered as unreacted substrate.

III. Analyses of N-(1-adamantyl methyl)-N'-cinnamoyl piperazine

Analytical data of N-(1-adamantyl methyl)-N'-cinnamoyl piperazine obtained in (II) are as follows. FIGS. 7, 8 and 9 illustrate Mass spectrum, IR absorption stectrum and NMR spectrum, respectively.

| (a) | Elementary analysis | | |
|---|---|---|---|
| | | Calculated ($C_{24}H_{32}N_2O$) | Found |
| | C: | 79.08% | 79.3% |
| | H: | 8.85% | 9.5% |
| | N: | 7.69% | 7.6% |
| (b) | Mass spectrum | | |
| | Calculated | | 364 |
| | Found Mass No. M⁺ | | 364 | c. IR absorption spectrum (KBr pellet)
1640 cm⁻¹ (amide), 1610, 1570, 1500, 1490, 1410, 1010 cm⁻¹ (phenyl), 960 cm⁻¹

(trans 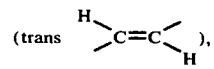 ), 760, 700 cm⁻¹ (mono-substituted phenyl), 1450, 1340, 1130 cm⁻¹ (adamantane)

d. NMR spectrum (solvent: CDCl₃)
8.48 τ(s. 6H, β-C$\underline{H}_2$), 8.32 τ(s. 6H, δ-C$\underline{H}_2$), 8.02 τ(s. 5H, γ-C$\underline{H}$ + C$\underline{H}_2$-N), 7.50 τ(t. J=4 Hz, 4H, b-C$\underline{H}_2$), 6.32 τ(t. J=4 Hz, 4H, a-C$\underline{H}_2$), 3.12 τ(d. J=16 Hz, 1H, $\underline{H}_{(2)}$), 2.32 τ(d. J=16 Hz, 1H, $\underline{H}_{(1)}$), 2.50 τ(m. 5H, phenyl)

e. Structure
From the results shown above, the structure of the compound can be deduced as follows:

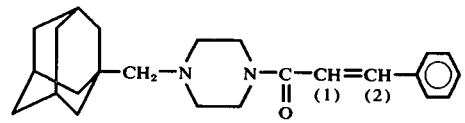

f. Melting point: 123°–125° C

EXAMPLE 4

Synthesis of N-(1-adamantyl methyl)-N'-cinnamyl piperazine

I. Reaction of N-(1-adamantyl methyl)-piperazine and cinnamyl chloride

Into 15 ml of isopropanol, 0.13 g (0.00055 mole) of N-(1-adamantyl methyl)-piperazine which was obtained in Example 3, (I)(4) and 0.057 g (0.00055 mole) of triethylamine were dissolved, and isopropanol soludion (3 ml) containing 0.08 g (0.00055 mole) of cinnamyl chloride was added dropwise at 0° C. After refluxing for 5 hrs., isopropanol was distilled away and residues were dissolved in 20 ml of chloroform. Subsequently, chloroform was washed with water, dehydrated and then was distilled away in vacuo. The residue thus obtained were subjected to silicia gel column chromatography (eluant: mixture of chloroform and methanol). Recrystallization from ethanol gave N-(1-adamantyl methyl)-N'-cinnamyl piperazine. Melting point of the product was 85°–87° C and the yield was 58%.

II. Reaction of N-cinnamyl piperazine and 1-adamantyl methyl halide

To a 10 ml autoclave, 1.6 g (0.008 mole) of N-cinnamyl piperazine which was obtained in Example 2, (I)(1), 1 g of 1-adamantyl methyl bromide obtained in Example 3(I)(2) and 0.43 g (0.004 mole) of anhydrous sodium carbonate were place and the atmosphere was replaced by argon, and the reaction was carried out at 200° C for 16 hours. After the reaction, it was brought to room temperature and 30 ml of chloroform was added, which was filtered, then washed with water. After dehydration of chloroform layer, chloroform was distilled away. The residues were subjected to silica gel column chromatography (eluant: mixture of chloroform and methanol). The product, N-(1-adamantyl methyl)-N'-cinnamyl piperazine was recrystallized from ethanol. Melting point of the product was 85°–88° C and the yield was 31%.

III. Reduction of N-(1-adamantane carbonyl)-N'-cinnamoyl piperazine

To 20 ml of tetrahydrofuran, 1 g of N-(1-adamantane carbonyl)-N'-cinnamoyl piperazine which was obtained in Example 1 (II) was dissolved and to this 0.24 g of lithium aluminum hydride powder were added gradually at 0° C. After refluxing for 4 hrs., it was cooled to 0° C and water was added to this at 0° C carefully to separate an organic solvent layer, subsequently the solvent was distilled away. The residues were dissolved in chloroform which was washed with water, dehydrated and then was distilled away. The residues were subjected to silica gel column chromatography (eluant: mixture of chloroform and methanol) and N-(1-adamantyl methyl)-N'-cinnamyl piperazine was obtained. Melting point of the product was 85°–87° C and the yield was 20%.

IV. Reduction of N-(1-adamantane carbonyl)-N'-cinnamyl piperazine

To 15 ml of tetrahydrofuran, 0.9 g (0.0025 mole) of N-adamantane carbonyl)-N'-cinnamyl piperazine which was obtained in Example 2 (II) were dissolved and to this, 0.14 g (0.0037 mole of lithium aluminum hydride powder were added at 0° C. After refluxing for 9 hrs., it was cooled to 0° C and 10 ml of water were added gradually to separate an organic solvent layer, which was dehydrated and was distilled away. Residues were subjected to silica gel column chromatography (eluants were mixtures of chloroform and methanol) and N-(1-adamantyl methyl)-N'-cinnamyl piperazine was recrystillized from ethanol. Melting point of the product was 85°–87° C and the yield was 55%.

V. Reduction of N-(1-adamantyl methyl)-N'-cinnamoyl piperazine

To 20 ml of tetrahydrofuran, 2 g (0.005 mole) of N-(1-adamantyl methyl)-N'-cinnamoyl piperazine which was obtained in Example 3(II) were dissolved and to this solution, 0.31 g (0.008 moles) of lithium aluminum hydride powder were added gradually at 0° C with stirring. After refluxing for 3 hrs., the reaction mixture was brought to 0° C and an organic solvent layer was separated by adding 10 ml of water. The organic solvent layer was washed with water, and dehydrated and then the solvent was distilled away in vacuo. Residues were subjected to silica gel column chromatography (eluants were mixtures of chloroform and methanol) and N-(1-adamantyl methyl)-N'-cinnamyl piperazine was recrystallized from ethanol. Melting point of the product was 85°–87° C and the yield was 40%.

VI. Analyses of N-(1-adamantyl methyl)-N'-cinnamyl piperazine

Analytical results on N-(1-adamantyl methyl)-N'-cinnamyl piperazine which was obtained in (I)–(V) are as follows. FIGS. 10, 11 and 12 illustrate Mass spectrum, IR absorption spectrum and NMR spectrum, respectively.

| (a) | Elementary analysis | |
|---|---|---|
| | Calculated | Found |
| C: | 82.23% | 82.36% |
| H: | 9.78% | 10.45% |
| N: | 7.99% | 7.98% |
| (b) | Mass spectrum | |
| | Calculated | 350 |
| | Found Mass No. M+ | 350 | c. IR absorption spectrum (KBr pellet)
1600, 1580, 1500, 1450, 1080, 1010 cm$^{-1}$ (phenyl), 970cm$^{-1}$

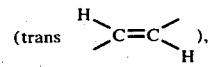

750, 700 cm$^{-1}$ (mono-substituted phenyl), 1450, 1350, 1150 cm$^{-1}$ (adamantane)

d. NMR spectrum (solvent: CDCl$_3$)
8.52 τ(s. 6H, β-CH$_2$), 8.36 τ(s. 6H, δ-CH$_2$), 8.08 τ(s. 5H, γ-CH + Ma—CH$_2$), 7.52τ(s. 8H, a-CH$_2$ + b-CH$_2$), 6.90 τ(d. J=4.0 Hz, 2H, Mc-CH$_2$), 3.70 τ(m. 2H, vinyl), 2.70 τ(m. 5H, phenyl)

e. Structure
From the results shown above, the structure of the compound can be deduced as follows:

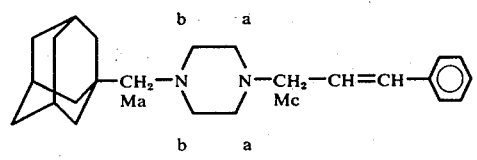

f. Melting point: 85°–87° C

EXAMPLE 5

Pharmacological effects of N-(1-adamantyl methyl)-N'-cinnamyl piperazine

The pharmacological effects of N-(1-adamantyl methyl)-N'-cinnamyl piperazine were compared with those of Cinnarizine which is commercially available as a cerebral vasodilator and the results of the comparison are as follows:

1. Effect on blood flow

The action on cerebral blood flow and muscular blood flow was examined with cats weighing about 3 kg. As a result, N-(1-adamantyl methyl)-N'-cinnamyl piperazine clearly increased blood flow of cerebral cortex at 1 mg/kg and its action was more significant than that induced by Cinnarizine 1 mg/kg.

Also, N-(1-adamantyl methyl)-N'-cinnamyl piperazine clearly increased blood flow of gastrocnemius muscle and its action was more significant than that of Cinnarizine.

2. Hypotensive action

Cinnarizine showed clear hypotensive action at 0.5 mg/kg, but N-(1-adamantyl methyl)-N'-cinnamyl piperazine showed hypotensive action at >5 mg/kg. Therefore the hypotensive action of this substance is clearly weaker than that of Cinnarizine and its safety is presumed to be high.

3. Effect on contraction of isolated smooth muscle

It was determined to what extent the action of contracting substances such as adrenalin, etc., on isolated smooth muscle is inhibited by administering N-(1-adamantyl methyl)-N'-cinnamyl piperazine or Cinnarizine. The result is as shown in the following Table.

| Contracting Substance | Test animal and organ | Compound | Effective concentration (g/ml) | Inhibitory rate (%) |
|---|---|---|---|---|
| Adrenalin $2.86 \times 10^{-6}$ g/ml | Vessels excised from guinea-pigs | N-(1-adamantyl methyl)-N-'-cinnamyl piperazine | $1 \times 10^{-5}$ | 3.10 |
| | | Cinnarizine | $1 \times 10^{-5}$ | 32.50 |
| Histamine $1.00 \times 10^{-7}$ g/ml | Small intestine excised from guinea-pigs | N-(1-adamantyl methyl)-N'-cinnamyl piperazine | $1 \times 10^{-4}$ | 95.0 |
| | | Cinnarizine | $1 \times 10^{-5}$ | 91.9 |
| $BaCl_2$ $2.00 \times 10^{-3}$ g/ml | Small intestine excised from guinea-pigs | N-(1-adamantyl methyl)-N'-cinnamyl piperazine | $1 \times 10^{-4}$ | 77.23 |
| | | Cinnarizine | $1 \times 10^{-5}$ | 25.2 |
| Acethylcholine $5.43 \times 10^{-4}$ g/ml | Small intestine excised from guinea-pigs | N-(1-adamantyl methyl)-N'-cinnamyl piperazine | $8.75 \times 10^{-6}$ | 25.0 |
| | | Cinnarizine | $2.30 \times 10^{-6}$ | 28.15 |

As the result of a experiments, N-(1-adamantyl methyl)-N'-cinnamyl piperazine was recognized to possess smooth muscle relaxing action.

4. Acute toxicity $LD_{50}$ values calculated by up and down method in mice and shown in the following table.

| Compound | Administration route | | $LD_{50}$ value (mg/kg) |
|---|---|---|---|
| N-(1-adamantyl methyl)-N(-cinnamyl piperazine | P.O. | *1 | >10,000 |
| | I.V. | *2 | 78.75 (75.4–82.1) |
| Cinnarizine | P.O. | | >1,000 |
| | I.V. | | 31.80 (22.7–40.9) |

*1 P.O. Oral administration
*2 I.V. Intravenous injection

5. Solubility (aptitude test as an injection)

For the purpose of examining the solubility of the new compound N-(1-adamantyl methyl)-N'-cinnamyl piperazine in an aqueous solution of tartaric acid, the aqueous solutions in which 2, 4, 6 and 8 times molar of tartaric acid based on 1 mol of the new compound were contained were prepared and the compound was added so that its concentration should be 0.25 weight percent to each aqueous solution. Each aqueous solution was heated to 80° C and allowed to cool to a room temperature (about 20° C), then the solubility was evaluated. As a result, the compound proved to be soluble in all of the above aqueous solutions of tartaric acid. In addition, the pH value of 0.25 weight percent aqueous solution of the compound prepared by using 2 times mol of tartaric acid based on 1 molar of the compound was 3.10 and when an alkali was added to the aqueous solution, crystals began to separate at pH 3.80.

6. Stability

After heating a 0.25 weight percent aqueous solution of the new compound N-(1-adamantyl methyl)-N'-cinnamyl piperazine prepared by using 2 times mol of tartaric acid based on 1 mol of this compound, the solution was allowed to cool to a room temperature (about 20° C). Then, the pH value was adjusted to 8–9 with 1/10 N aqueous solution of sodium hydroxide. The sample available to be extracted with chloroform and another sample left at a room temperature for 7 days, were then extracted with chloroform in the same way were subjected to thin layer chromatography for comparison, and as a result, the compound proved to be unaffected. No change was seen in infrared absorption spectrum and nuclear magnetic resonance spectrum.

From the above result, the compound proved to exist stably in an aqueous solution of tartaric acid.

Figure 1:
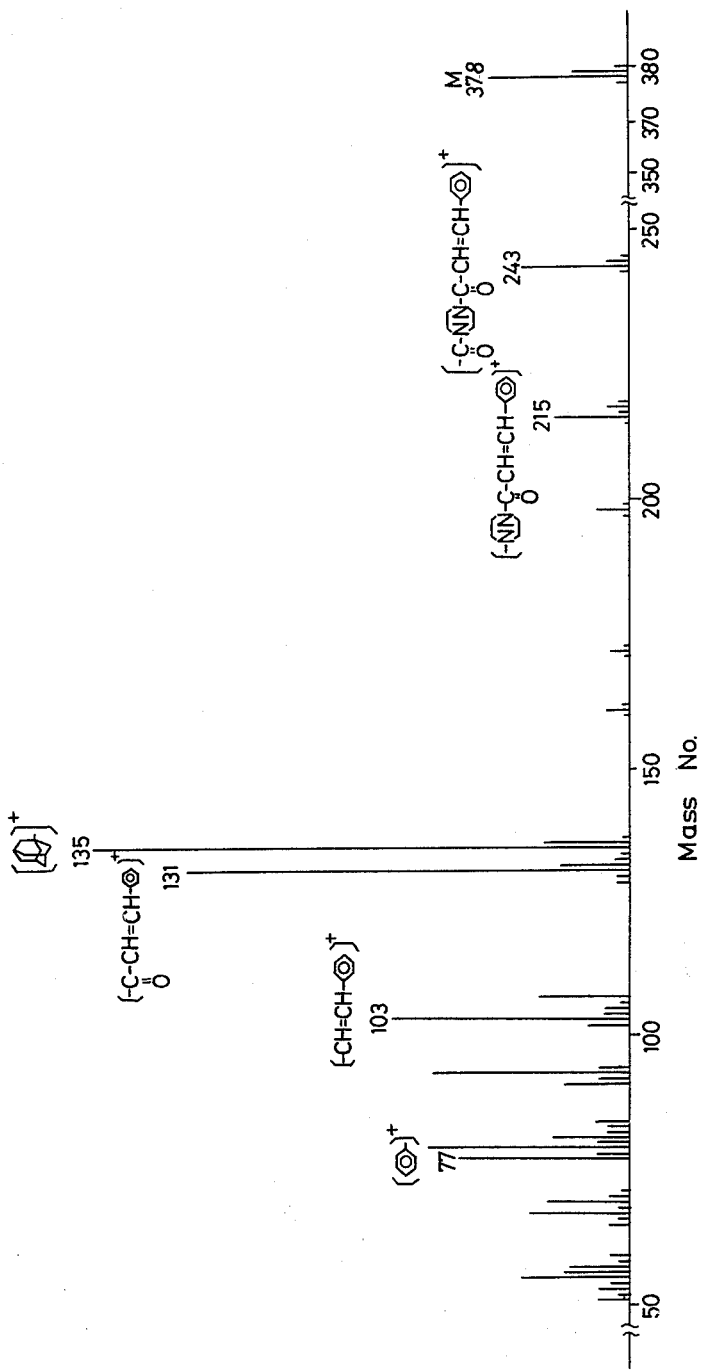
FIG. 1, FIG. 2 and FIG. 3 show respectively mass spectrum, infrared absorption spectrum and nuclear magnetic resonance spectrum of N-(1-adamantane carbonyl)-N'-cinnamoyl piperazine.
Figure 2:
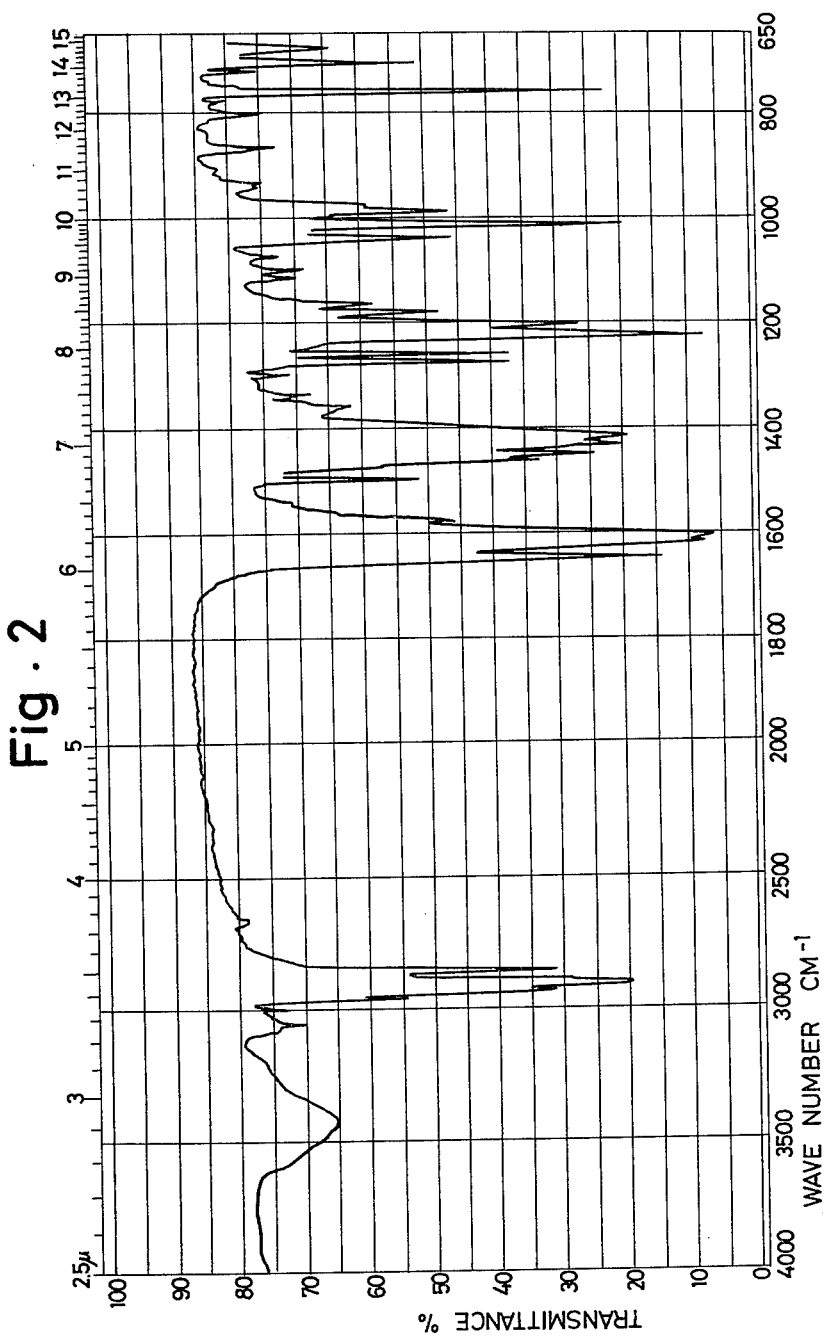
Figure 3:
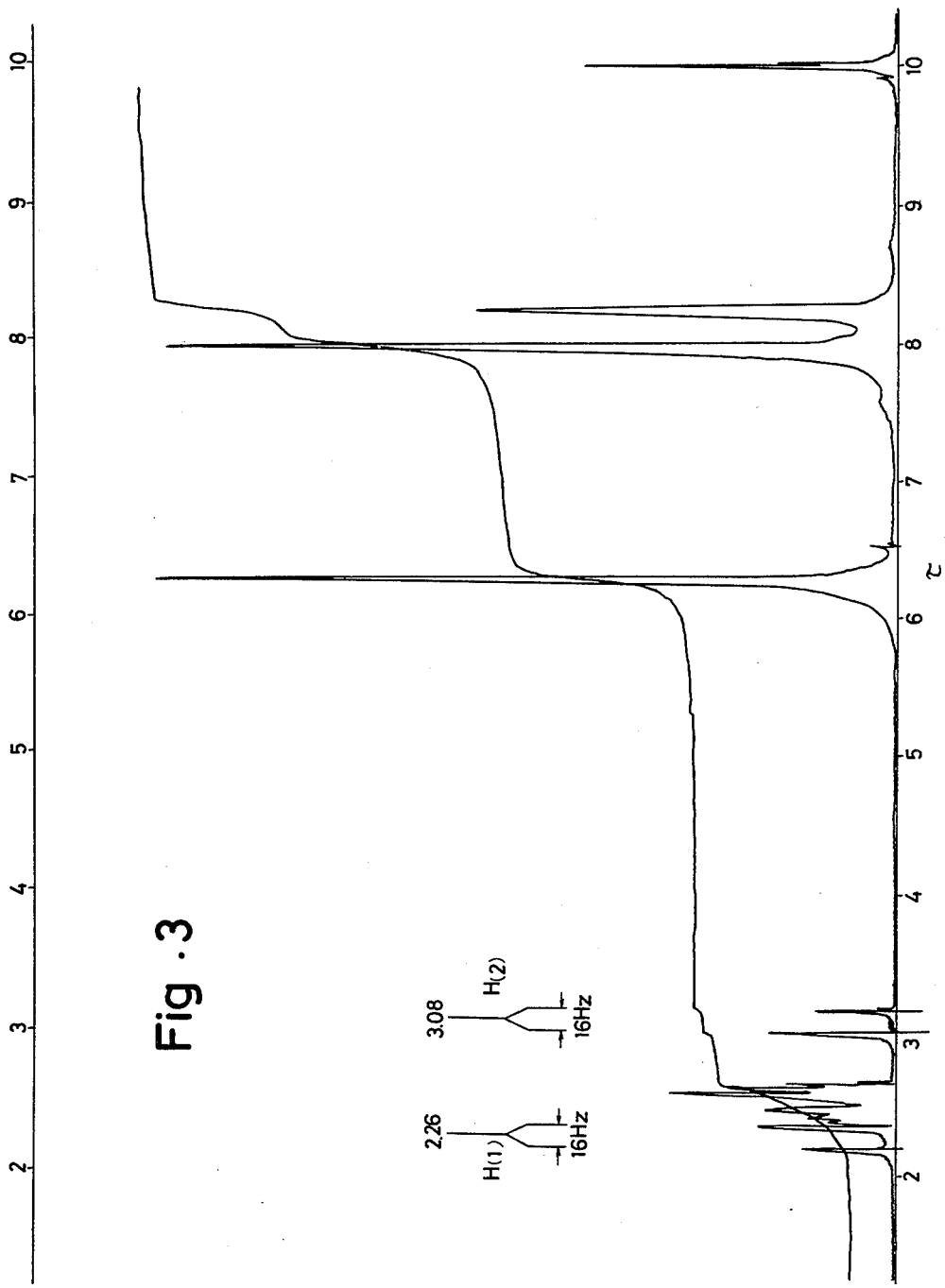
Figure 4:
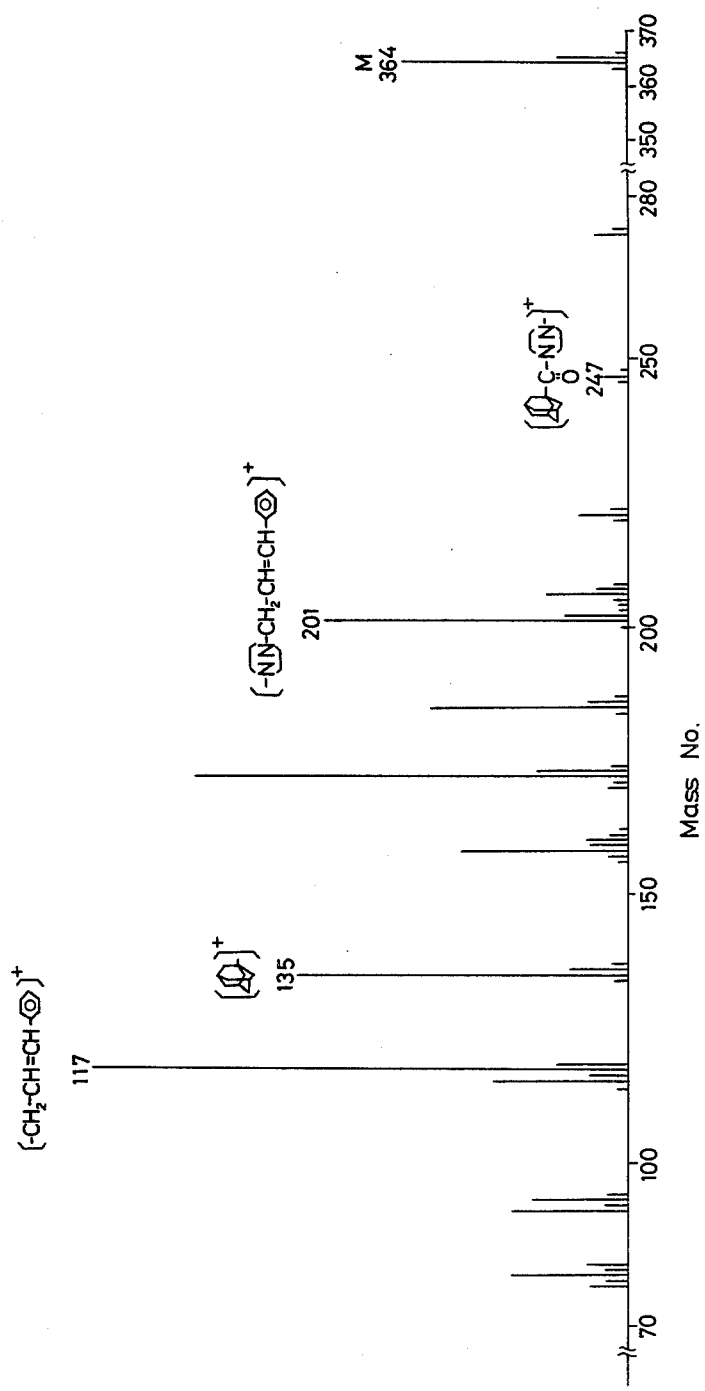
FIG. 4, FIG. 5 and FIG. 6 show respectively mass spectrum, infrared absorption spectrum and nuclear magnetic resonance spectrum of N-(1-adamantane carbonyl)-N'-cinnamyl piperazine.
Figure 5:
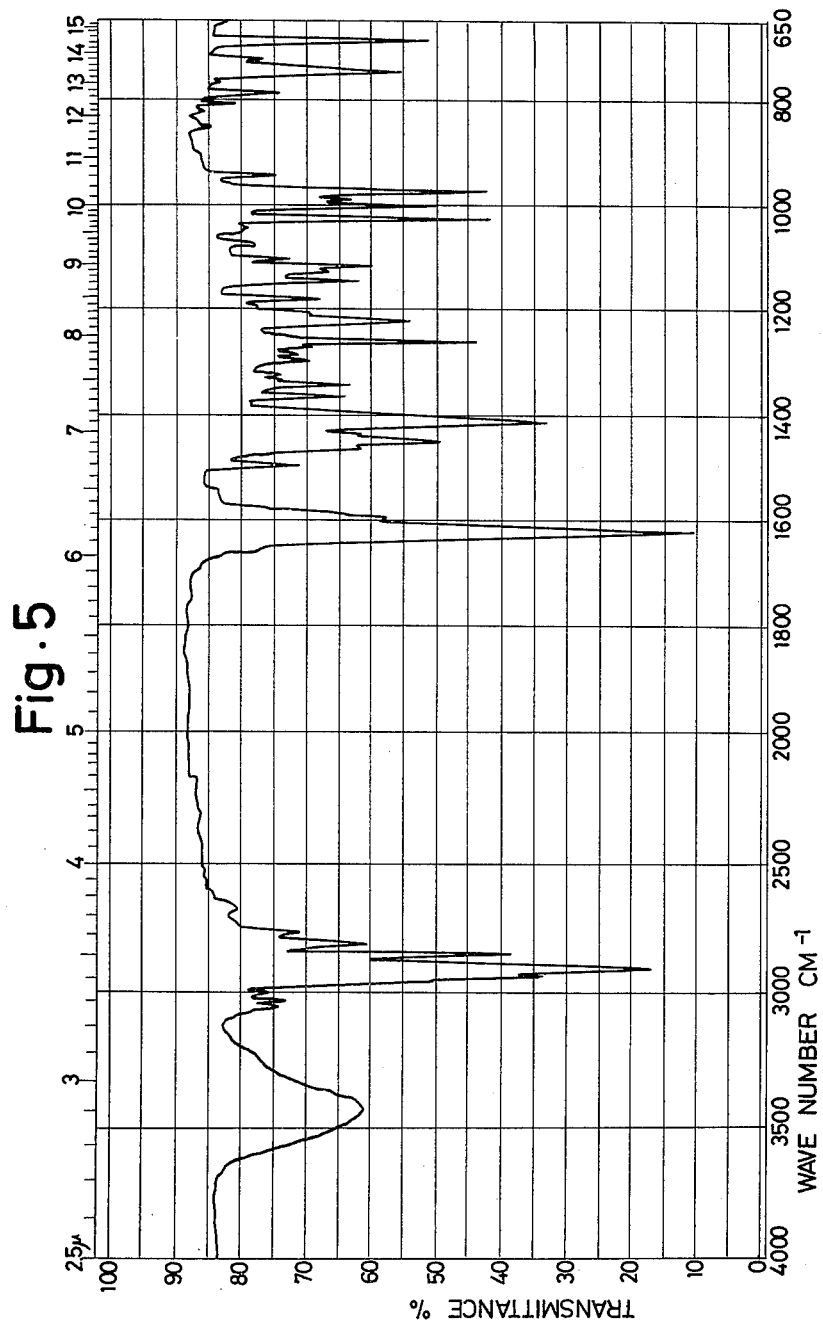
Figure 6:
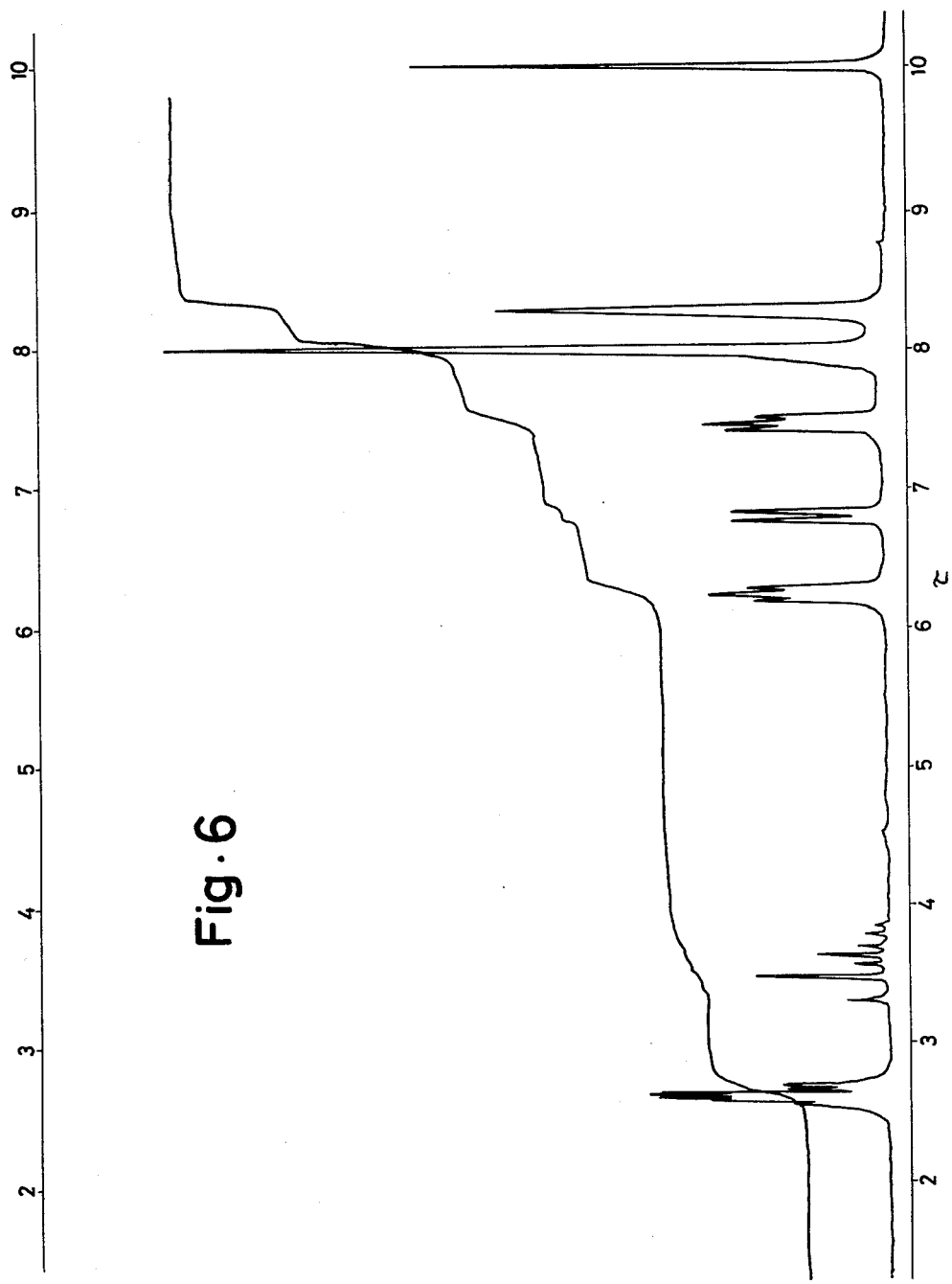
Figure 7:
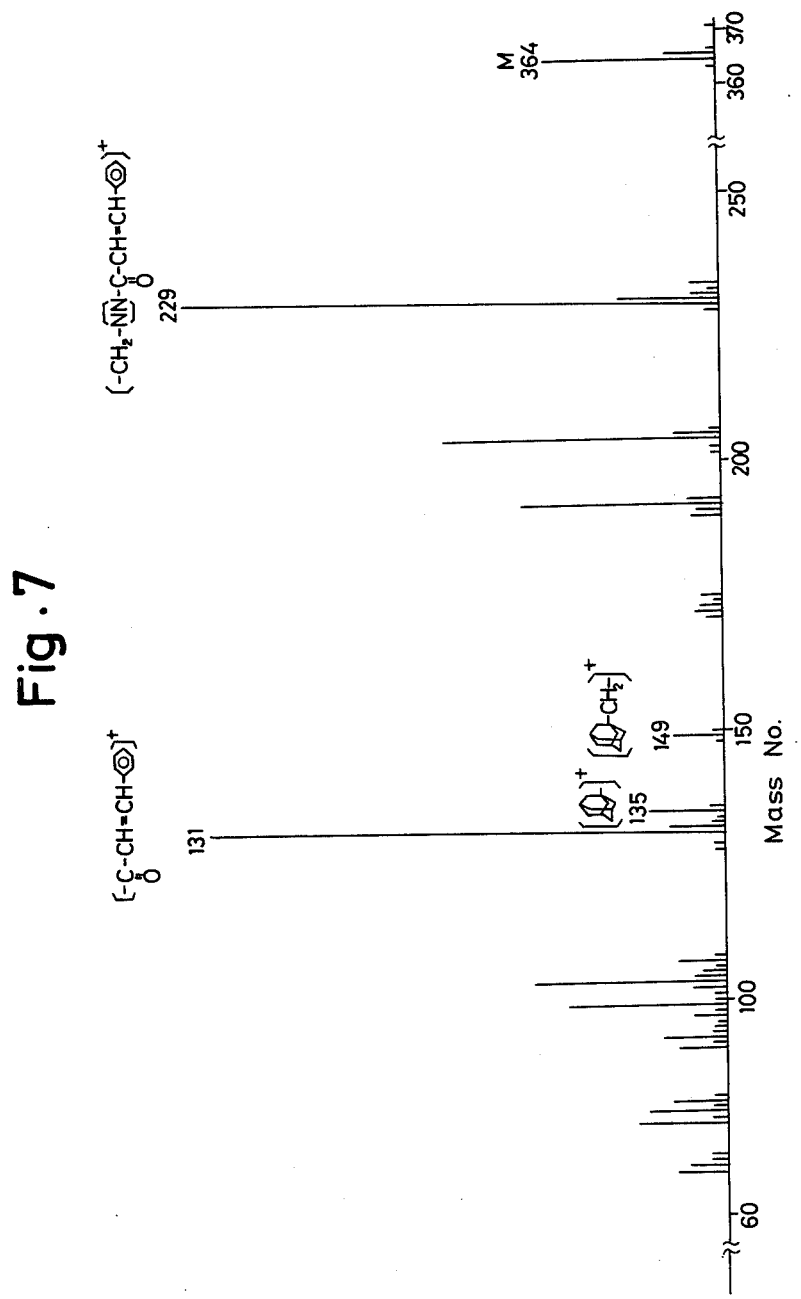
FIG. 7, FIG. 8 and FIG. 9 show respectively mass spectrum, infrared absorption spectrum and nuclear magnetic resonance spectrum of N-(1-adamantyl methyl)-N'-cinnamoyl piperazine.
Figure 8:
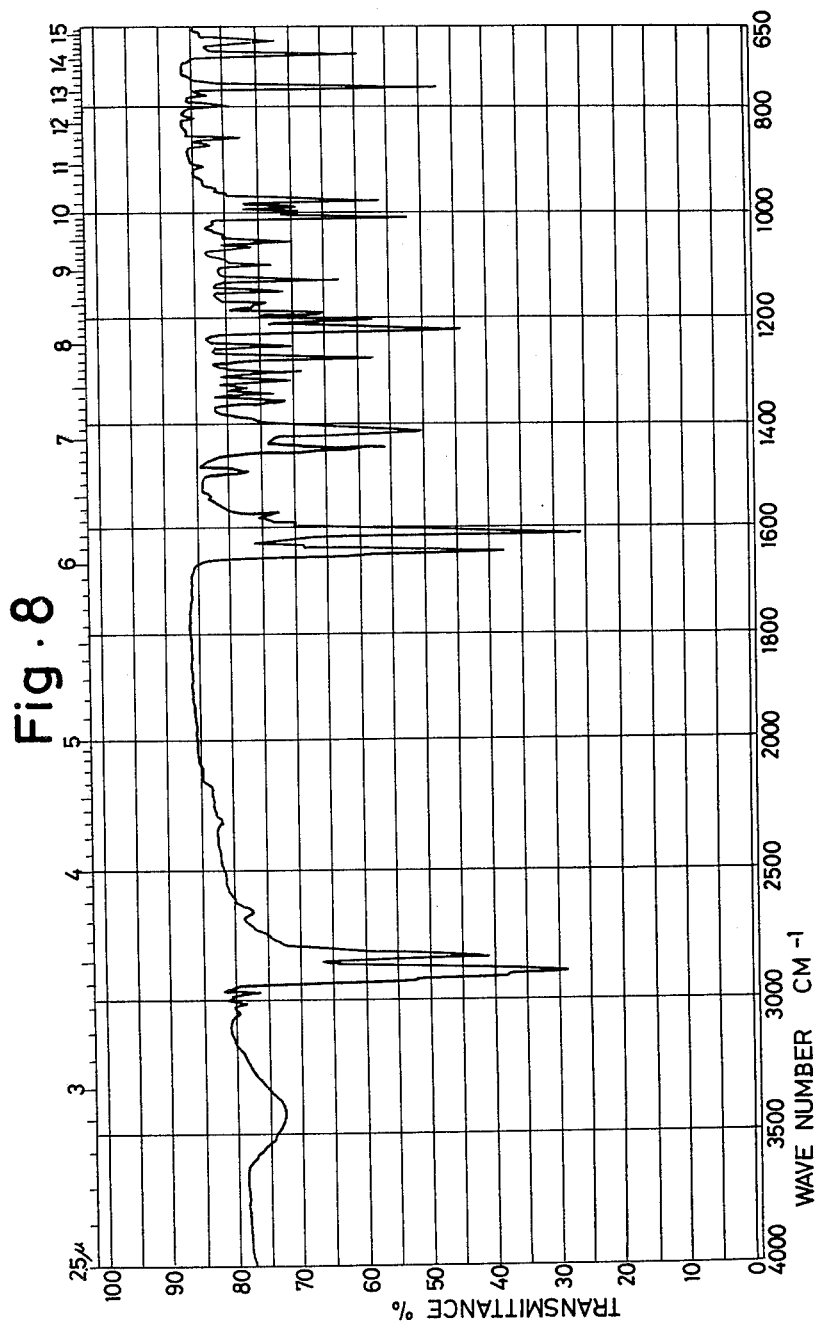
Figure 9:
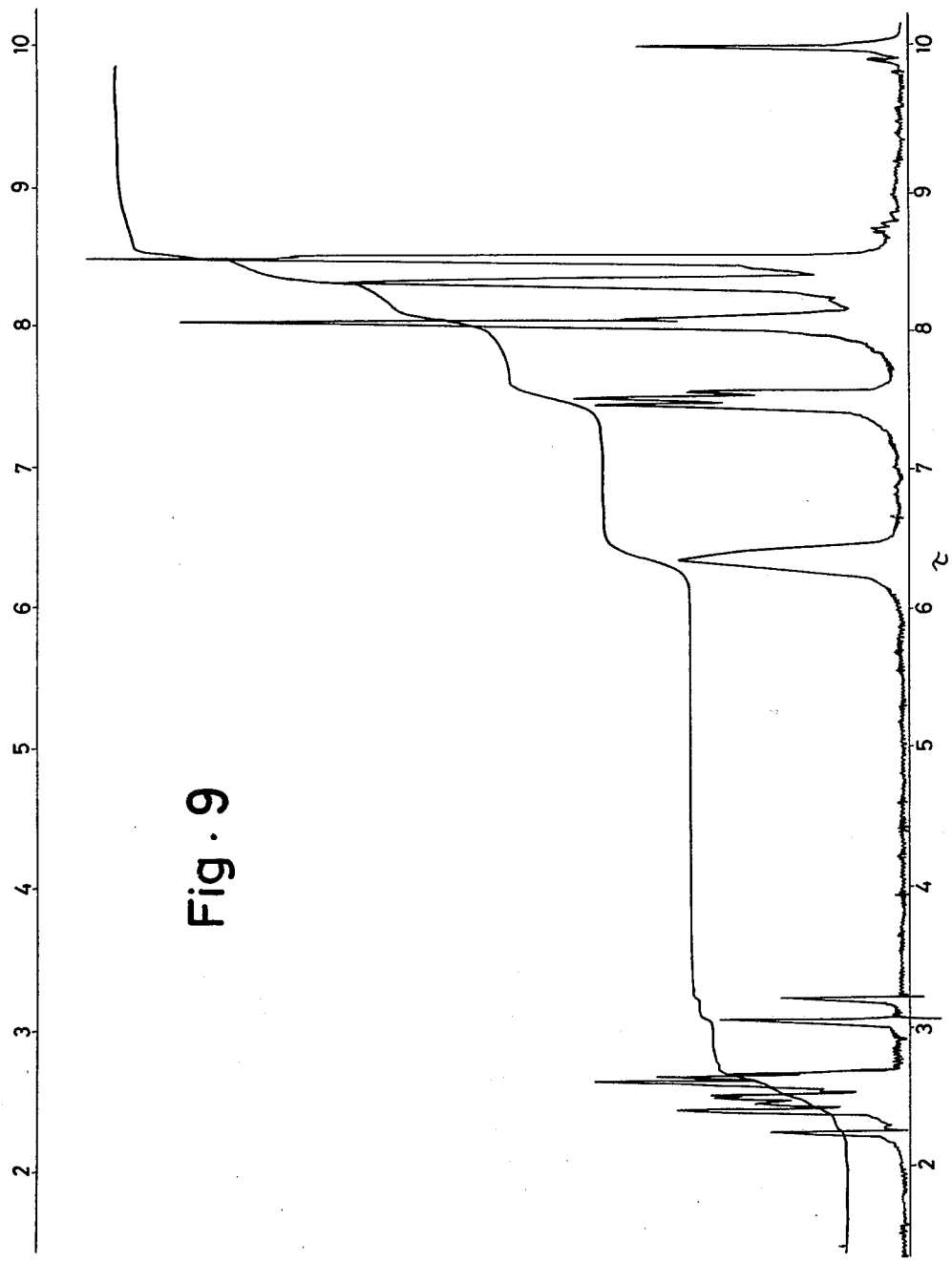
Figure 10:
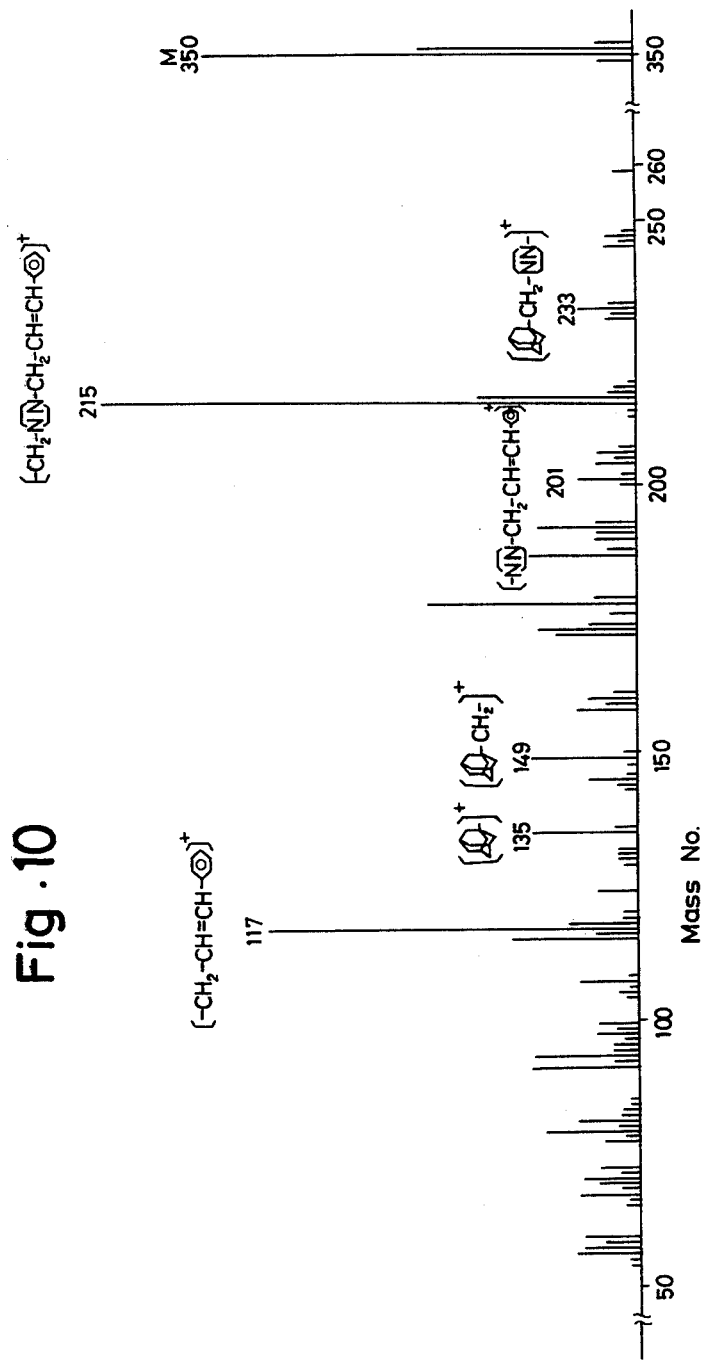
FIG. 10, FIG. 11 and FIG. 12 show respectively mass spectrum, infrared absorption spectrum and nuclear magnetic resonance spectrum of N-(1-adamantyl methyl)-N'-cinnamyl piperazine.
Figure 11:
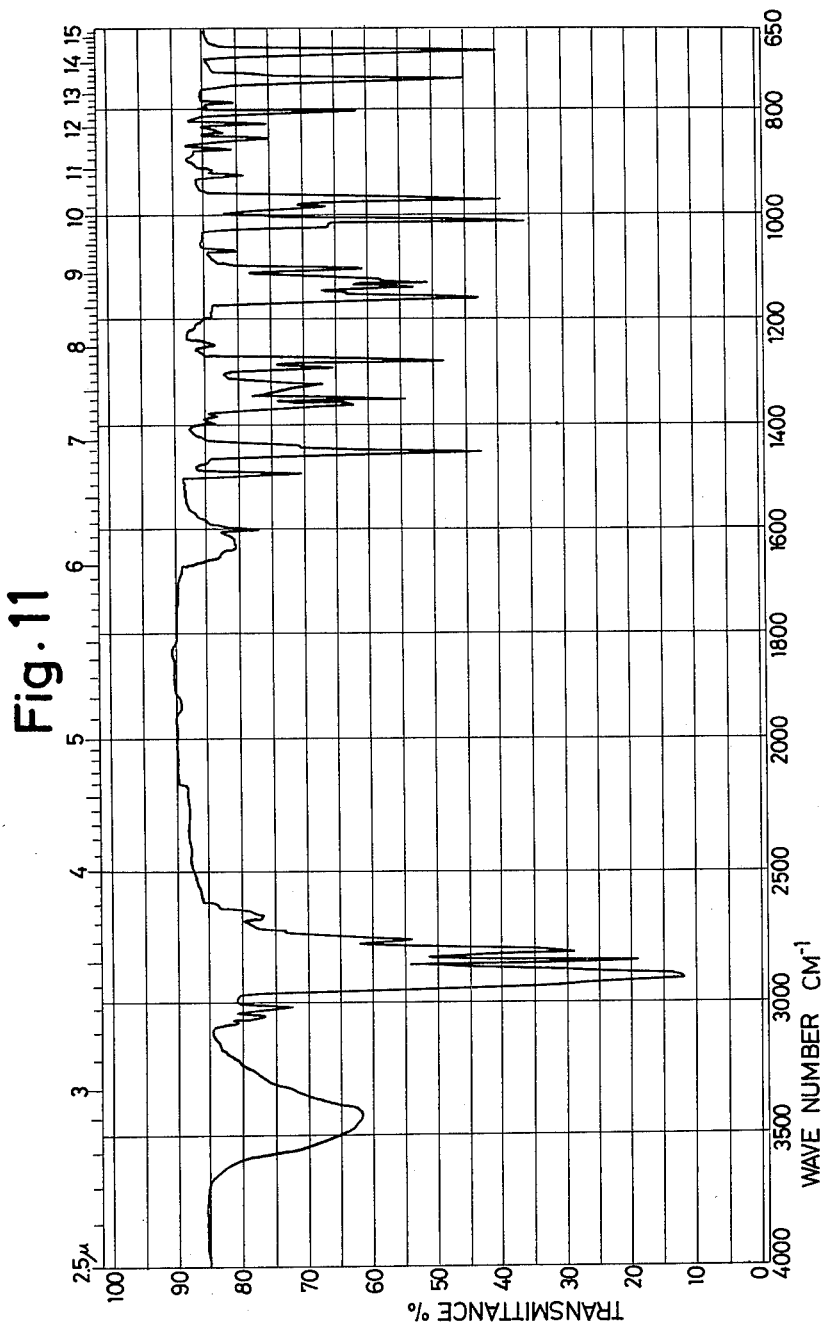
Figure 12:
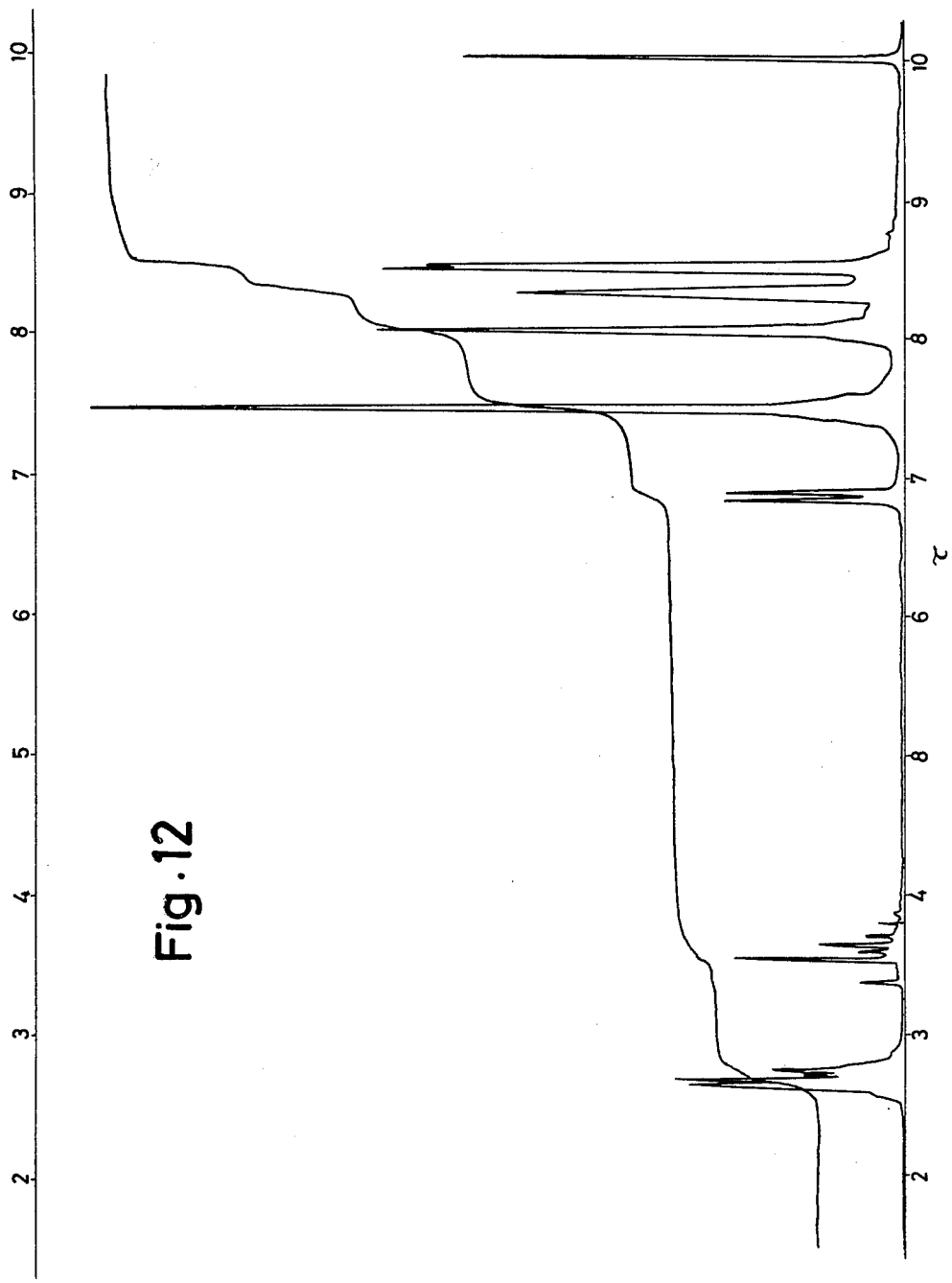

What is claimed is:

1. Adamantane derivatives represented by the formula

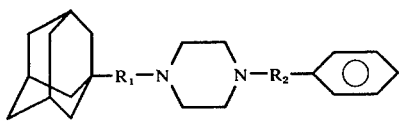

wherein $R_1$ is

or —$CH_2$— and $R_2$ is

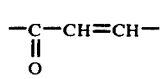

or —$CH_2$—CH=CH—.

2. Adamantane derivative of claim 1, wherein said derivative is N-(1-adamantane carbonyl)-N'-cinnamoyl piperazine represented by the formula

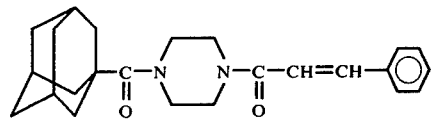

3. Adamantane derivative of claim 1, wherein said derivative is N-(1-adamantane carbonyl)-N'-cinnamyl piperazine represented by the formula

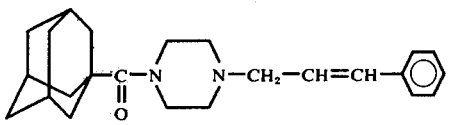

4. Adamantane derivative of claim 1, wherein said derivative is N-(1-adamantyl methyl)-N'-cinnamoyl piperazine represented by the formula

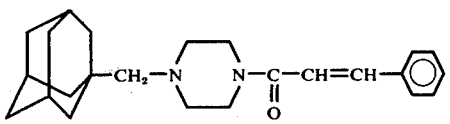

5. Adamantane derivative of claim 1, wherein said derivative is N-(1-adamantyl methyl)-N'-cinnamyl piperazine represented by the formula

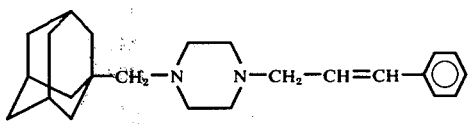

* * * * *

UNITED STATES PATENT AND TRADEMARK OFFICE
CERTIFICATE OF CORRECTION

PATENT NO. : 4,001,223
DATED : January 4, 1977
INVENTOR(S) : MICHIO SUGIMOTO et al It is certified that error appears in the above-identified patent and that said Letters Patent are hereby corrected as shown below:

Column 1, lines 12-13: delete "...expected...synthesizing them..." and replace with --- ...considered to be promising medicines or intermediates for synthesizing medicines... ---.

Column 6, line 50: delete "proceeding of".

Column 16, lines 10-11: delete "stectrum" and replace with --- spectrum ---.

UNITED STATES PATENT AND TRADEMARK OFFICE
CERTIFICATE OF CORRECTION

PATENT NO. : 4,001,223
DATED : January 4, 1977
INVENTOR(S) : MICHIO SUGIMOTO et al It is certified that error appears in the above-identified patent and that said Letters Patent are hereby corrected as shown below:

Column 3, line 65: replace "moles" with --- molar ---.

Column 6, lines 34-35: delete "the product hydrating" and replace with --- hydrating the product ---.

Column 16, line 24: replace "960 $cm^{-1}$" with --- 970 $cm^{-1}$ ---.

Column 17, line 48: after "(0.0037 mole", insert --- ) ---.

Column 19, line 57: replace ">1,000" with --->10,000 ---.

Signed and Sealed this

Tenth Day of January 1978

[SEAL]

Attest:

RUTH C. MASON
*Attesting Officer*

LUTRELLE F. PARKER
*Acting Commissioner of Patents and Trademarks*